United States Patent [19]

Bennett

[11] Plant 5,081

[45] Aug. 9, 1983

[54] MINIATURE ROSE PLANT

[76] Inventor: Cecilia L. D. Bennett, 489 Minot Ave., Chula Vista, Calif. 92010

[21] Appl. No.: 365,450

[22] Filed: Apr. 5, 1982

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by the pointed petal's giving the bloom a starlike appearance.

1 Drawing Figure

1

The present invention relates to a new and distinct variety of a hardy, dwarf, miniature bush plant of the miniature class; the variety being primarily characterized as an apricot blend.

The variety is further characterized by:

An abundance of blooms with a starlike appearance, usually blooming one to a stem.

No discernable fragrance.

Buds and flowers comparable in size to "Sheri Anne", a miniature introduced by Sequoia Nurseries in 1973. (U.S. Plant Pat. No. 3,826.)

The plant ranges in height from 12 to 8 inches. The branches are very slender giving the plant an open, airy appearance. Grows equally well in the hothouse or outdoors.

The present variety of miniature rose was originated by me at Tiny Petal's Nursery, located at Chula Vista, Calif., under careful observation, and is a cross of "Sheri Anne" a miniature as the pollen plant, and "Contempo" a florabunda, (U.S. Plant Pat. No. 3,102) an orange blend, introduced by Armstrong Nurseries in 1971, as the seed parent.

Subsequent to origination of the variety I successfully reproduced it by cuttings and bud-grafts at Tiny Petal's Nursery located at aforesaid with reproductions coming true in all respects.

The color photographs illustrate the variety.

Referring now specifically to the new and distinct variety of miniature rose plant, the following is a detailed description thereof in outline; all major color plate identification being by reference to the British Colour Council Horticultural Colour Chart.

Type: Hardy; dwarf; compact; seedling; greenhouse; outdoors; cut flowers; garden decoration; potted plant.

Class: Miniature; Variety name: "Twinkle Twinkle".

Flowers borne: One to a stem, or clusters of three to five blooms as plant matures.

Quantity of bloom: Abundant both in the hothouse or outdoors.

Bud:

*Peduncle.*—Slender; erect; reddish; 1¼ to 1½ inches in length.

*Hairs.*—Very minute; reddish.

*Before calyx breaks.*—Size small.

*Form.*—Slender; tapered with sepals extending well out over the end of the bud wrapping around each other in a twisting effect.

*Color.*—Medium green with a very reddish tinge.

2

*As calyx breaks; color.*—Medium reddish with a creamish color blending to a faint green at the base of the petal's . Opens well in all weather.

Bloom:

*Size when fully open.*—Averaging from 1½ to 1¾ inches in diameter.

*Petalage.*—Double — averaging from 25 to 35 petals, arranged regularly.

*Form.*—Center petals shorter than the outer petals. Opens slowly, petals reflex gently. Open flower reveals stamens.

Petals: Good substance; matt surface topside and underside.

*Shape.*—Outside petals, broad lanceolate with acute tip; intermediate petals, elongated with acute tip. inner petals, short elongated with acute tip.

Color: Newly opened flower from plant grown at Chula Vista, Calif.

Outer petals: Topside surface jasper red O 18/2 page 107 blending down to an egyptian buff 407/3 page 122 down to orange buff 507/3 page 133.

Outer petals:

*Underside surface.*—Egyptian buff 407/3 page 122.

Intermediate petals:

*Topside surface.*—Outer edge jasper red O18/2 page 107 blending down to orange buff 507/3 page 133.

Intermediate petals:

*Underside surface.*—Orange buff 407/3 page 122.

Center petals:

*Topside surface.*—Outer edge jasper red O18/2 page 107 blending to orange buff 507/3 page 133.

Center petals:

*Underside surface.*—Orange buff 507/3 page 133.

Behavior: Opens well in all weather.

*Form.*—Decorative: Color — orange color fades to a near white and the jasper red deepens as the bloom ages. The bloom holds its starlike form and beauty for a week to ten days.

Reproductive organs:

*Stamens.*—Abundant, arranged evenly around pistils.

*Filament.*—Varying lengths.

*Anthers.*—Well formed.

*Pollen.*—Abundant.

*Pistils.*—About 20 to 25.

*Styles.*—Short, irregular.

*Ovaries.*—All encased in calyx.

*Hips.*—None.

*Sepals.*—Long spear shaped, tapered then a slight flaring.

*Seeds.*—None.

Foliage:

*Leaves.*—Compound of five and seven. small: glossy.

*Leaflets.*—Shape: broad; arrow shaped.

*Margin.*—Very serrated.

*Color.*—Medium green, edges reddish.

Rachis: Medium length; underside smooth.

*Stipule.*—Medium length; medium width.

Growth:

*Habit.*—Dwarf; bushy; much branched.

*Growth.*—Vigorous.

*Canes.*—Long; slender.

*Main stem.*—Color — medium green and reddish.

*Thorns.*—Small; very slender; hooked downward; reddish.

*Prickles.*—None.

*Branches.*—Color — medium green and reddish. Thorns very sparce.

The miniature rose plant and it's flowers as herein described may vary in slight detail due to climatic, soil and cultural conditions under which the variety may be grown; the present description being of the variety as grown at Chula Vista, Calif.

I claim:

1. A new and distinct variety of miniature rose plant of hardy, dwarf, bushy, much branched habit, substantially as illustrated and decribed, characterized by buds and flowers.

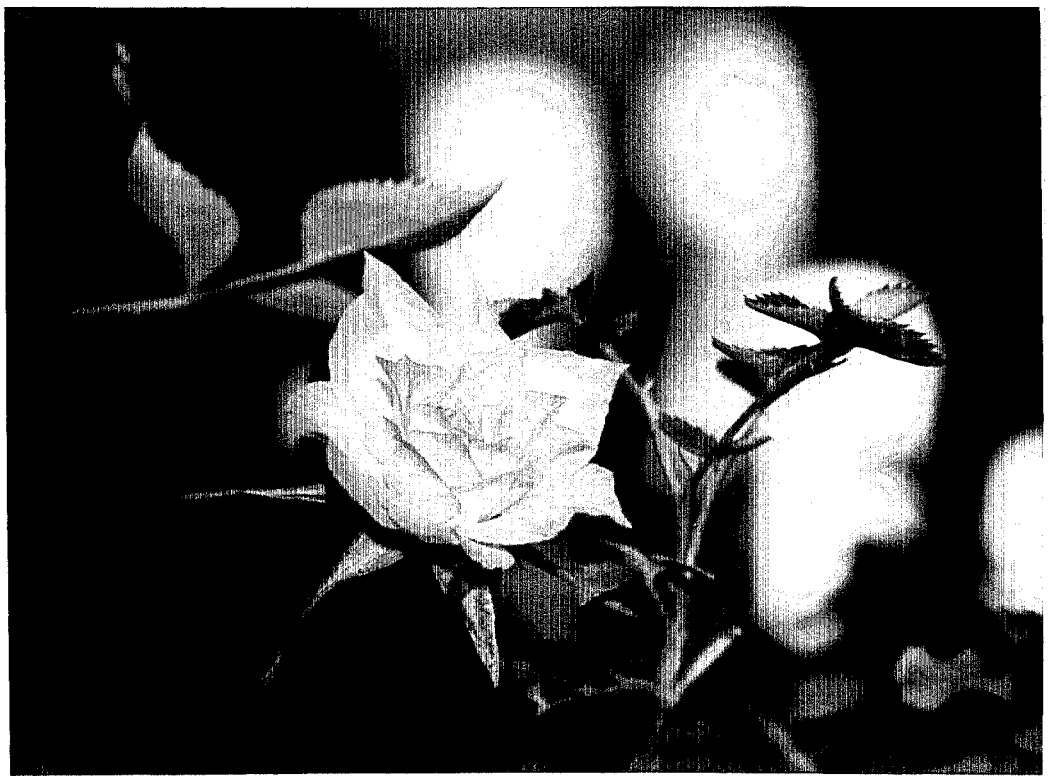

* * * * *